Figure 1:
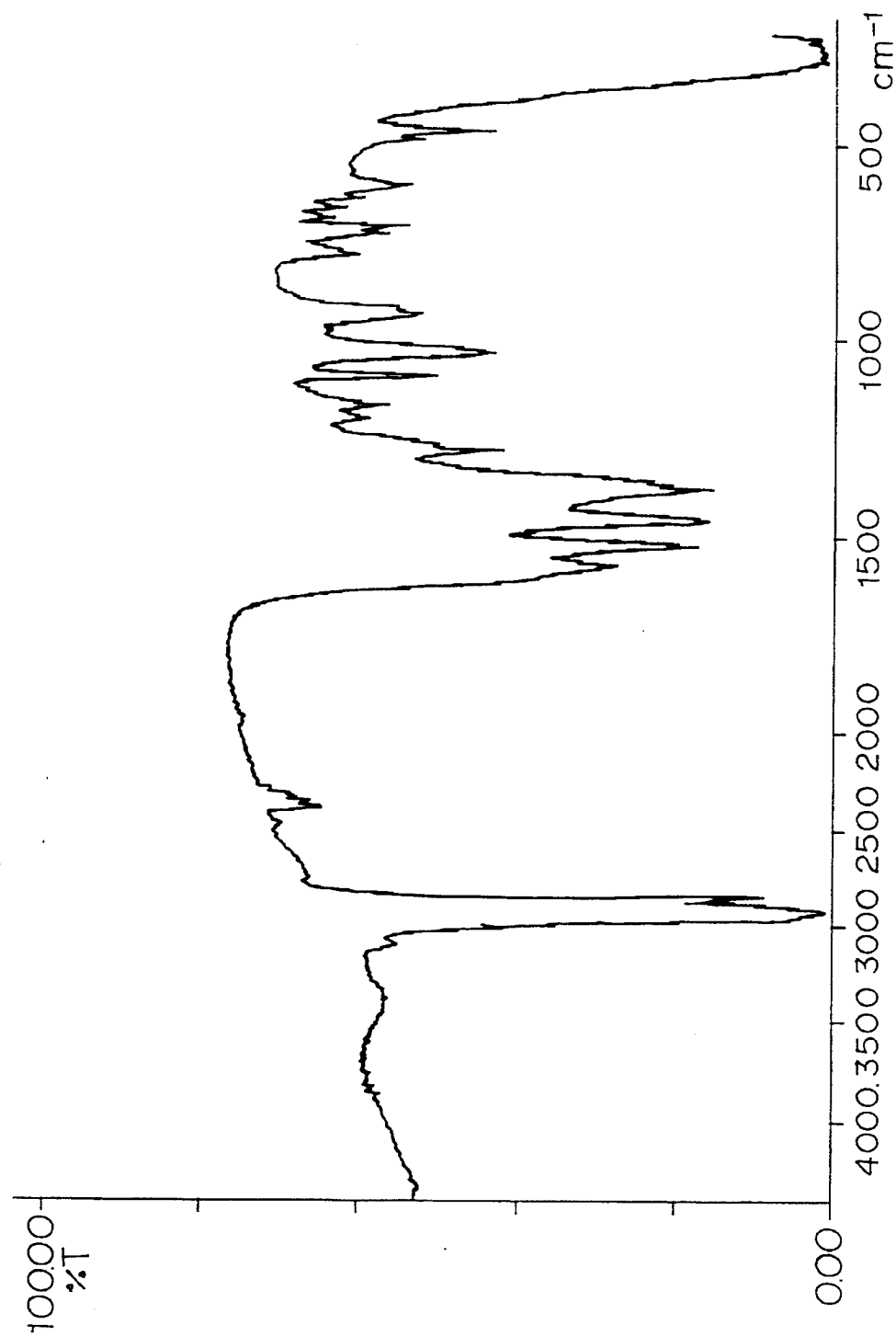

United States Patent [19]

Tanaka et al.

[11] Patent Number: 5,491,272
[45] Date of Patent: Feb. 13, 1996

[54] METHOD FOR OLIGOMERIZING AN ALPHA-OLEFIN

[75] Inventors: Eiji Tanaka, Kurashiki; Hisao Urata, Tokyo; Toshiyuki Oshiki, Yokohama, all of Japan

[73] Assignee: Mitsubishi Chemical Corporation, Tokyo, Japan

[21] Appl. No.: 121,864

[22] Filed: Sep. 17, 1993

[30] Foreign Application Priority Data

| Sep. 17, 1992 | [JP] | Japan | 4-247811 |
| Nov. 24, 1992 | [JP] | Japan | 4-313646 |
| Nov. 24, 1992 | [JP] | Japan | 4-313647 |
| Nov. 25, 1992 | [JP] | Japan | 4-315247 |

[51] Int. Cl.$^6$ ................................................. C07C 2/02
[52] U.S. Cl. .................... 585/520; 585/500; 585/502; 585/521; 585/522; 585/523; 585/527; 585/530
[58] Field of Search ................................. 585/500, 502, 585/520, 521, 522, 523, 527, 530

[56] References Cited

U.S. PATENT DOCUMENTS

| 3,347,840 | 10/1967 | Manyik et al. . |
| 4,668,838 | 5/1987 | Briggs . |
| 4,853,356 | 8/1989 | Briggs . |
| 5,198,563 | 3/1993 | Reagen et al. . |
| 5,376,612 | 12/1994 | Reagen et al. . |

FOREIGN PATENT DOCUMENTS

| 0417477 | 3/1991 | European Pat. Off. . |
| 0416304 | 3/1991 | European Pat. Off. . |
| 0537609 | 4/1993 | European Pat. Off. . |
| 0548805 | 6/1993 | European Pat. Off. . |
| 3-128904 | 5/1991 | Japan . |
| 93/0350 | 1/1993 | South Africa . |

*Primary Examiner*—Asok Pal
*Assistant Examiner*—E. D. Irzinski
*Attorney, Agent, or Firm*—Oblon, Spivak, McClelland, Maier & Neustadt

[57] ABSTRACT

A method for oligomerizing an α-olefin in the presence of a catalyst comprising a specific chromium compound including chromium atom and pyrrolyl group and an alkylaluminum compound, wherein the α-olefin is contacted to the chromium compound and the alkylaluminum compound without preliminarily contacting the chromium compound to either the α-olefin or the alkylaluminum compound.

33 Claims, 1 Drawing Sheet

METHOD FOR OLIGOMERIZING AN ALPHA-OLEFIN

The present invention relates to a method for oligomerizing an α-olefin, particularly ethylene, by means of a catalyst comprising a specific chromium compound and an alkylaluminum compound, to selectively obtain a product composed mainly of a trimer in good yield.

Heretofore, it has been known to oligomerize an α-olefin such as ethylene by means of a catalyst composed of a combination of a chromium compound and an organoaluminum compound.

For example, Japanese Examined Patent Publication No. 18707/1968 discloses a method for preparing 1-hexene and polyethylene from ethylene by a catalyst system comprising a Cr-containing Group VIB transition metal compound of the formula MXn and a polyhydrocarbyl aluminum oxide. Further, Japanese Unexamined Patent Publication No. 128904/1991 and V. W. Seidel and W. Reichardt, Z. Anorg. Allg. Chem., 404, 225 (1974) disclose a method for producing a chromium-containing compound having a chromium-pyrrolyl bond by reacting a chromium salt and a metal pyrrolide in tetrahydrofuran or dimethoxyethane containing an oxygen atom as an electron pair donor element. Further, Japanese Unexamined Patent Publication No. 128904/1991 discloses a method for trimerizing an α-olefin by means of a catalyst obtained by a combination of this chromium-containing compound with a metal alkyl or a Lewis acid.

However, among the above methods, the one disclosed in Japanese Examined Patent Publication No. 18707/1967 has a problem that the amount of polyethylene formed simultaneously with 1-hexene is substantial, and if it is attempted to reduce the amount of the polyethylene, the overall activities tend to deteriorate.

On the other hand, the method disclosed in Japanese Unexamined Patent Publication No. 128904/1991 has drawbacks such that the operation for isolating the chromium compound is cumbersome, and it is extremely difficult to selectively obtain a single chromium compound, and that the catalytic activities are poor for the oligomerization reaction of an α-olefin using the chromium-containing compound as a catalyst.

Further, it has been known that a compound containing an electron pair donor element forms a complex in coordination with a transition metal element such as a chromium element. In the process for producing the above-mentioned chromium-containing compound, a chromium salt and a metal pyrrolide are reacted by using a compound containing an electron pair donor element as a solvent, whereby the compound containing an electron pair donor element tends to compete with the metal pyrrolide in coordination with the chromium salt thereby to form a mixture of complex products wherein the electron pair donor compound ligand and the pyrrolyl group are coordinated to the chromium element in various proportions. Further, according to the amount of an alkylaluminum compound, the selectivity of 1-hexene among hexenes produced tends to change, which is believed to be attributable to the coordinated electron pair donor compound contained in the chromium compound.

The present inventors have conducted extensive researches to solve the above-mentioned problems of the conventional methods and as a result, have accomplished the present invention.

The present invention provides a method for oligomerizing an α-olefin by means of a catalyst system comprising a chromium compound having at least one chromium-pyrrolyl bond and an alkylaluminum compound, wherein the α-olefin is contacted with the chromium compound and the alkylaluminum compound without preliminarily contacting the chromium compound to either the α-olefin or the alkylaluminum compound, and/or wherein the alkylaluminum compound is used in an amount of at least 20 mmol per g of the chromium compound.

In the accompanying drawing, FIG. 1 is an IR spectrum of the powder of chromium compound 6 obtained in Catalyst Preparation Example 6.

Now, the present invention will be described in detail with reference to the preferred embodiments.

The chromium compound containing a chromium-pyrrolyl bond, to be used in the present invention, may be the one which contains a chromium atom and a pyrrolyl group, and may have other organic or inorganic groups, and it may further contain other metals. In the present invention, such a chromium compound may be obtained as a mixture of compounds of metals of Groups IA, IIA, IIIB or IVB of the Periodic Table when such a chromium compound is prepared by the reaction of a chromium salt with a metal pyrrolide, as described hereinafter. In the present invention, such a mixture is also included in the chromium compound containing a chromium-pyrrolyl bond.

In the present specification, a specific chromium compound indicates the following each chromium compound, 1. a chromium compound having at least one chromium-pyrrolyl bond,
2. a chromium compound prepared by the reaction of a chromium salt with a compound containing a pyrrolyl group in a hydrocarbon solvent.

In the present invention, the chromium compound containing a chromium-pyrrolyl bond, can be obtained by reacting a chromium salt and a compound containing a pyrrolyl group. Namely, for example, it can be obtained by reacting the chromium salt with a compound containing a pyrrolyl group in an electron pair donor solvent.

Here, the chromium salt may be represented by the general formula $CrX_n$ wherein X is an organic or inorganic group, and n is an integer of from 1 to 6, preferably 2 or 3, provided that when n is more than 1, the plurality of X may be the same or different. The organic group includes, for example, a hydrocarbon group, a carbonyl group, an alkoxy group, a carboxyl group, a β-diketonate group, a β-ketocarboxylic group, a β-ketoester group and an amide group. The carbon number of the organic group is usually from 1 to 30, and the hydrocarbon group includes, for example, an alkyl group, a cycloalkyl group, an aryl group, an alkylaryl group and an aralkyl group. The inorganic group may, for example, be a halogen, nitrate, sulfate or oxide. Preferably, the chromium salt is a halide, such as chromous chloride, chromic chloride, chromous bromide, chromic bromide, chromous iodide, chromic iodide, chromous fluoride or chromic fluoride, particularly preferably chromous chloride or chromic chloride. Further, a complex composed of such a chromium salt and an electron pair donor, such as an ether complex, an ester complex, a ketone complex, an aldehyde complex, an alcohol complex, an amine complex, a nitrile complex, a phosphine complex or a thioether complex of a halogenated chromium, specifically $CrCl_3 \cdot 3THF$, $CrCl_3 \cdot 3dioxane$, $CrCl_3 \cdot (CH_3CO_2n\text{---}C_4H_9)$, $CrCl_3 \cdot (CH_3CO_2C_2H_5)$, $CrCl_3 \cdot 3(i\text{---}C_3H_7OH)$, $CrCl_3 \cdot 3[CH_3(CH_2)_3CH(C_2H_5)CH_2OH]$, $CrCl_3 \cdot 3pyridine$, $CrCl_3 \cdot 2(i\text{---}C_3H_7NH_2)$, $[CrCl_3 \cdot 3MeCN] \cdot MeCN$ (MeCN=acetonitrile), $CrCl_3 \cdot 3PPh_3$ ($PPh_3$=triphenylphosphine), $CrCl_2 \cdot 2THF$, $CrCl_2 \cdot 2pyridine$, $CrCl_2 \cdot 2[(C_2H_5)_2NH)_2]$, $CrCl_2 \cdot 2MeCN$ (MeCN=acetonitrile), $CrCl_2 \cdot 2[P(CH_3)_2PH]$ (Ph= phenyl group), may also be employed.

The compound containing a pyrrolyl group is the one derived from pyrrole or a pyrrole derivative. The pyrrole derivative includes, for example, 2,5-dimethylpyrrole, 3,4-dimethylpyrrole, 3,4-dichloropyrrole, 2,3,4,5-tetrachloropyrrole, 2-formylpyrrole, 2-acetylpyrrole and 2-acylpyrrole. The compound derived from pyrrole includes, for example, a metal pyrrolide. The metal is selected from Groups IA, IIA, IIIB and IVB. A preferred metal pyrrolide may, for example, be lithium pyrrolide, sodium pyrrolide, potassium pyrrolide or cesium pyrrolide. Further, instead of such a metal pyrrolide, pyrrole or a pyrrole derivative itself, may also be employed.

The electron pair donor solvent may be selected among nitrogen-, oxygen-, phosphorus- and sulfur-containing compounds. The nitrogen-containing compound may, for example, be a nitrile, an amine or an amide and may specifically be acetonitrile, pyridine, dimethylpyridine, dimethylformamide, N-methylformamide, aniline, nitrobenzene, tetramethyldiaminomethane, hexamethyldisilazane or pyrrolidone. The oxygen-containing compound may, for example, be an ester, an ether, a ketone, an alcohol or an aldehyde and may specifically be ethyl acetate, methyl acetate, tetrahydrofuran, dioxane, diethyl ether, dimethoxyethane, diglyme, triglyme, acetone, methyl ethyl ketone, methanol, ethanol or acetaldehyde. The phosphorus-containing compound may, for example, be hexamethylphosphoramide, hexamethylphosphorus triamide, triethylphosphite, tributylphosphine oxide or triethylphosphine. The sulfur-containing compound may, for example, be carbon disulfide, dimethylsulfoxide, tetramethylenesulfone, thiophene or dimethylsulfide. Among the foregoing electron pair donor solvents, ethers are preferred. Among them, tetrahydrofuran, diethyl ether and dimethoxyethane are more preferred.

As a method for reacting the chromium salt and the metal pyrrolide in the electron pair donor solvent, the chromium salt and the metal pyrrolide are mixed at an optional ratio and reacted usually under atmospheric pressure preferably in the absence of an oxygen molecule. The reaction temperature may be at an optional level, but the reaction is preferably conducted under reflux of the solvent. If desired, the reaction may be conducted under irradiation with ultrasonic waves. The reaction time is usually from 30 minutes to 48 hours.

After completion of the reaction, by-products are removed by filtration, and then an excess electron pair donor solvent is preferably removed. As a method for removing the electron pair donor solvent, it is possible to employ a method of removing it under reduced pressure or by circulating an inert gas at high temperature or at ordinary temperature, or a method wherein a solvent other than the electron pair donor solvent in which the chromium compound is insoluble, is added, and then the formed precipitate of the chromium compound is collected by filtration and washed with the added solvent to remove the electron pair donor solvent. As the solvent other than the electron pair donor solvent, a linear or alicyclic saturated hydrocarbon such as pentane, hexane, heptane or cyclohexane, an aromatic hydrocarbon such as benzene, toluene or xylene, a linear chlorinated hydrocarbon such as chloroform, methylene chloride, dichloroethane or tetrachloroethane, or a chlorinated aromatic hydrocarbon such as chlorobenzene or dichlorobenzene, may, for example, be mentioned. However, it is preferred to employ a linear or alicyclic saturated hydrocarbon.

Another method for obtaining the chromium compound containing at least one chromium-pyrrolyl bond to be used in the present invention, is a method of reacting a chromium salt and/or complex soluble in a solvent other than the electron pair donor solvent, with a metal pyrrolide. As the solvent other than the electron pair donor solvent, the one used for the removal of the electron pair donor solvent as described above, may be employed.

The chromium salt and/or complex soluble in the solvent other than the electron pair donor solvent may, for example, be the above-mentioned complex of a halogenated chromium and an electron donor, such as an ether complex, an ester complex, a ketone complex, an aldehyde complex, an alcohol complex, an amine complex, a nitrile complex, a phosphine complex or a thioether complex of a halogenated chromium, specifically $CrCl_3 \cdot 3THF$, $CrCl_3 \cdot 3$dioxane, $CrCl_3 \cdot (CH_3CO_2n-C_4H_9)$, $CrCl_3 \cdot (CH_3CO_2C_2H_5)$, $CrCl_3 \cdot 3(i-C_3H_7OH)$, $CrCl_3 \cdot 3[CH_3(CH_2)_3CH(C_2H_5)CH_2OH]$, $CrCl_3 \cdot 3$pyridine, $CrCl_3 \cdot 2(i-C_3H_7NH_2)$, $[CrCl_3 \cdot 3MeCN] \cdot MeCN$ (MeCN=acetonitrile), $CrCl_3 \cdot 3PPh_3$ ($PPh_3$=triphenylphosphine), $CrCl_2 \cdot 2THF$, $CrCl_2 \cdot 2$pyridine, $CrCl_2 \cdot 2[(C_2H_5)_2NH]$, $CrCl_2 \cdot 2MeCN$ (MeCN=acetonitrile) or $CrCl_2 \cdot 2[P(CH_3)_2Ph]$ (Ph=phenyl group). Further, it may be a chromium β-diketonate, a chromium carboxylate, a chromium-carbonyl complex, various cyclopentadienyl complexes of chromium, a chromium-alkyl complex or a chromium-phenyl complex, specifically $Cr[CH_3COCH=C(O-)CH_3]_3$, $Cr(CH_3(CH_2)_3CH(C_2H_5)CO_2]_3$, $Cr(CO)_6$, $CpCrCl_2$ (Cp=cyclopentadienyl group), $(Cp*CrClCH_3)_2$ (Cp*=pentamethylcyclopentadienyl group), $(CH_3)_2CrCl$ or $CrPhCl_2 \cdot THF_3$.

As a method for reacting the chromium salt and/or complex and the metal pyrrolide in the solvent other than the electron pair donor solvent, the chromium salt and/or complex and the metal pyrrolide are mixed at an optional ratio and reacted usually under atmospheric pressure preferably in the absence of an oxygen molecule. If desired, the reaction may be conducted under irradiation with ultrasonic waves. The reaction temperature may be at a level from −100° C. to the boiling point of the solvent depending upon the types of the chromium salt and/or complex and the metal pyrrolide. The reaction time is usually from 30 minutes to 48 hours.

After completion of the reaction, by-products may be removed by filtration. However, without such removal, the reaction product may be used directly for the oligomerization reaction of an α-olefin. Further, without removing the solvent, the reaction product may be supplied directly for the oligomerization reaction of an α-olefin. When the reaction solvent is to be removed, it may be distilled off under reduced pressure or by circulating an inert gas at a high temperature or an ordinary temperature, or a solvent in which the formed chromium compound is insoluble, is added, and then the precipitate containing the chromium compound is collected by filtration and washed with the added solvent to remove the reaction solvent.

Another method for obtaining a specific chromium compound, which catalyzes the oligomerization of α-olefin, particularly ethylene, in the present invention is that the reaction of a chromium salt with a compound containing a pyrrolyl group is conducted in a hydrocarbon solvent as the solvent other than the electron pair donor solvent. In this method, the chromium compound can be prepared in a good yield even without adopting the above-mentioned cumbersome isolation operation compared when the reaction of a chromium salt with a metal pyrrolide is conducted in an electron pair donor one. When an α-olefin, particularly ethylene, is oligomerized on using such a chromium compound prepared in a hydrocarbon solvent, it is possible to obtain hexenes having a high selectivity of 1-hexene. Besides, in spite of the change in the reaction conditions such that the amount of the alkylaluminum compound is reduced, the selectivity of 1-hexene in the resulting hexenes can be maintained at a high level.

In the present invention, it is essential that such a chromium compound contains both chromium atom and pyrrolyl group. The chromium compound prepared by the reaction of a chromium salt with a compound containing a pyrrolyl group in a hydrocarbon solvent may be obtained as a mixture of chromium atom, a pyrrolyl group, other organic or inorganic groups, and/or metals of IA, IIA, IIIB, or IVB of the Periodic Table. Such a mixture is also included in the chromium compound in the present invention.

The chromium compound can be obtained by reacting a chromium salt and a compound containing a pyrrolyl group in a hydrocarbon solvent.

In detail, when the chromium salt and the compound containing a pyrrolyl group are reacted in the hydrocarbon solvent, the chromium salt is preferably soluble in the hydrocarbon solvent. As such a compound, a chromium β-diketonate, a chromium carboxylate, a chromium β-ketocarboxylate, a chromium-amide complex, a chromium-carbonyl complex, various cyclopentadienyl complexes of chromium, a chromium-alkyl complex or a chromium-phenyl complex may, for example, be mentioned. Particularly preferred is a chromium β-diketonate, a chromium-carboxylate or a chromium β-ketocarboxylate. More specifically, it may, for example, be $Cr(CO)_6$, $CpCrCl_2$ (Cp=cyclopentadienyl group), $(Cp*CrClCH_3)_2$ (Cp*=pentamethylcyclopentadienyl group), $(CH_3)_2CrCl$, chromium (III) acetylacetonate, chromium (III) 2,2,6,6-tetramethyl-3,5-heptanedionate, chromium (III) 2-ethylhexanoate, chromium (III) naphthenate, chromium (III) methyl acetoacetate, or chromium (II) bis(trimethylsilyl)amide.

As the hydrocarbon solvent, a hydrocarbon compound and a halogenated hydrocarbon compound may, for example, be mentioned as typical examples. More specifically, it includes, for example, aliphatic and alicyclic hydrocarbon compounds such as n-hexane, cyclohexane, n-heptane and n-octane, aliphatic and alicyclic unsaturated hydrocarbon compounds such as 1-hexene, cyclohexene and cyclooctene, aromatic hydrocarbon compounds such as toluene, benzene and xylene, and halogenated hydrocarbon compounds such as carbon tetrachloride, chloroform, methylene chloride, chlorobenzene and dichlorobenzene. Among them, aliphatic, alicyclic and aromatic hydrocarbons are preferred.

The compound containing a pyrrolyl group is exemplified as the same described hereinbefore.

As a method for reacting the chromium salt and the compound containing a pyrrolyl group such as a metal pyrrolide in the hydrocarbon solvent, the chromium salt and the compound containing a pyrrolyl group such as a metal pyrrolide are mixed at an optional ratio and reacted usually under atmospheric pressure preferably in the absence of an oxygen molecule. The reaction temperature may be at a level of from −100° C. to the boiling point of the solvent depending upon the types of the chromium salt and/or complex and the compound containing a pyrrolyl group. If desired, the reaction may be conducted under irradiation with ultrasonic waves. The reaction time is usually from 30 minutes to 48 hours.

After completion of the reaction, by-products may be removed by filtration, but the chromium compound may be obtained by removing the solvent from the reaction product without removing such by-products. Further, without removal of the solvent, the reaction product may directly be used for the oligomerization reaction of an α-olefin. As a method for removing the reaction solvent or the washing solution, it is possible to employ a method wherein the solvent for the washing solution is distilled off under reduced pressure or by circulating an inert gas at a high temperature or at room temperature, or a method wherein after completion of the reaction, the product is left to stand still, followed by filtration or removal of the supernatant, then the residue is washed preferably with a hydrocarbon compound which has low boiling point such as n-hexane. After removing the washing solution, the chromium compound is obtained.

In the present invention, the specific chromium compounds can be used as supported on a carrier such as an inorganic oxide. However, in such a case, the amount of polymer formed tends to increase. Therefore, it is preferably used simply in combination with the alkylaluminum compound without employing such an operation. Namely, according to the method of the present invention, high catalytic activities can be obtained without employing a cumbersome operation of supporting on a carrier. Further, the method is free from such a problem that the total amount of the catalyst used (the total amount of the carrier and the chromium catalyst and the alkylaluminum compound) is increased by the use of the carrier.

In the present invention, the oligomerization of an α-olefin is conducted by the combination of the specific chromium compound thus obtained, with an alkylaluminum compound. The alkylaluminum compound is preferably an alkylaluminum compound of the following formula:

$$R^1_m Al(OR^2)_n H_p X_q \quad (1)$$

wherein each of $R^1$ and $R^2$ which may be the same or different, is a $C_{1-15}$, preferably $C_{1-8}$, hydrocarbon group, X is a halogen atom, $0<m\leq3$, $0\leq n<3$, $0\leq p<3$, $0\leq q<3$, and $m+n+p+q=3$. For example, alkylaluminum compounds of the following formulas (2) to (7) may be mentioned:

a trialkylaluminum compound of the formula:

$$R^1_3 Al \quad (2)$$

wherein $R^1$ is as defined above;

a halogenated alkylaluminum compound of the formula:

$$R^1_m AlX_{3-m} \quad (3)$$

wherein $R^1$ and X are as defined above, and $1.5\leq m<3$;

an alkoxyalkylaluminum compound of the formula:

$$R^1_m Al(OR^2)_{3-m} \quad (4)$$

wherein $R^1$ and $R^2$ are as defined above, and $0<m<3$, preferably $1.5\leq m<3$;

an alkylaluminum hydride compound of the formula:

$$R^1_m AlH_{3-m} \quad (5)$$

wherein $R^1$ is as defined above, and $0<m<3$, preferably $1.5\leq m<3$;

an aluminoxane of the formula:

$$R^1_2 Al(OAl)_m OAlR^1_2 \quad (6)$$

or

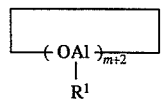
(7)

In the formulas (6) and (7), $R^1$ is as defined above, and m is an integer of from 0 to 30, preferably at least 10.

Specifically, trimethylaluminum, triethylaluminum, triisobutylaluminum, diethylaluminum chloride, diethylaluminum ethoxide, diethylaluminum hydride, methylaluminoxane and isobutylaluminoxane may, for example, be mentioned. Among them, a trialkylaluminum is preferred, since only a small amount of polymer formed as by-product.

To conduct the oligomerization using the specific chromium compound obtained by the reaction in a hydrocarbon solvent, the amount of the alkylaluminum compound to be used per g of the chromium compound is at least 0.1 mmol, but preferably more than 5 mmol, so that the catalytic activities and the selectivity for the trimer will be improved. The method for producing the chromium compound in a hydrocarbon solvent has a merit in that as compared with the case where a chromium compound produced in an electron pair donor solvent is employed, the amount of the alkylaluminum compound to be used may be small, and yet the selectivity of the resulting 1-hexene among hexenes produced will not decrease.

In the present invention, the oligomerization reaction is conducted usually by using a solvent. As such a solvent, a linear or alicyclic saturated hydrocarbon such as butane, pentane, hexane, heptane, octane, cyclohexane, methylcyclohexane or decalin, an aromatic hydrocarbon such as benzene, toluene, xylene, ethylbenzene or tetralin, a chain chlorinated hydrocarbon such as chloroform, methylene chloride, dichloroethane, trichloroethane or tetrachloroethane, or chlorinated aromatic hydrocarbon such as chlorobenzene or dichlorobenzene, may, for example, be used. Among these solvents, a linear or alicyclic saturated hydrocarbon is preferred. Further, the α-olefin as the starting material for the reaction itself, or an α-olefin other than the main starting material for reaction, may be used as the solvent. As such an α-olefin, the one having from 4 to 30 carbon atoms may be employed, but the one which is liquid at room temperature, is particularly preferred. In a case where the oligomerization of an α-olefin is conducted by specifying the contacting method of the catalyst and the amount of the alkylaluminum compound to be used, it is preferred to use an alicyclic hydrocarbon among these solvents, since high catalytic activities can thereby be obtained. Further, in a case where the oligomerization reaction is conducted by prescribing the concentration of the chromium compound, it is preferred to use a chain saturated hydrocarbon such as butane, pentane, hexane, heptane or octane.

The α-olefin as the starting material to be used in the present invention, is a substituted or unsubstituted α-olefin having from 2 to 30 carbon atoms. Specific examples include ethylene, propylene, 1-butene, 1-pentene, 1-hexene, 1-octene, 3-methyl-1-butene and 4-methyl-1-pentene. The present invention is particularly suitable for the oligomerization of ethylene, whereby 1-hexene can selectively be obtained in good yield.

The temperature for the oligomerization reaction is usually from 0° to 250° C., preferably from 0° to 150° C., and the pressure is usually from atmospheric pressure to 250 kg/cm$^2$, but it may sufficiently be not more than 100 kg/cm$^2$. The retention time is usually within a range of from 1 minute to 20 hours, preferably from 0.5 to 6 hours.

The reaction may be conducted by a batch system, a semi-continuous system or a continuous system. The apparatus for the reaction is not particularly limited. For example, a tubular reactor or an agitation tank type reactor may be employed.

In the present invention, it is necessary either to contact the α-olefin to the chromium compound having at least one chromium-pyrrolyl bond and the alkylaluminum compound without preliminarily contacting the chromium compound to the α-olefin and the alkylaluminum compound, or to use the alkylaluminum compound in an amount at least 20 mmol per g of the chromium compound. However, when both of the above conditions are satisfied, the largest effects can be obtained with respect to the catalytic activities and the selectivity for trimer.

When the above-mentioned contacting method is employed, the amount of the above alkylaluminum compound to be used against the chromium compound having at least one chromium-pyrrolyl bond may be at any level so long as it is at least 5 mmol per g of the chromium compound or at least 25 mmol per g of chromium metal. As a specific contacting method, the reaction of batch system can be conducted by a method wherein the alkylaluminum compound is present in a solvent, and the chromium compound and the α-olefin are simultaneously introduced thereto, or a method wherein firstly, the α-olefin and the alkylaluminum compound are contacted, and then the chromium compound is introduced thereto. The reaction of continuous system can be conducted by a method wherein the respective components are supplied to the reactor directly and independently, or a method wherein the respective components are supplied and transported to a reactor through e.g. pipes connected to the reactor, in the order to realize the same contacting state as in the above-mentioned method for batch system. Under the conditions of the present invention, the interaction between the alkylaluminum compound and the α-olefin is so small that the above-mentioned various contacting methods can be regarded as substantially the same method.

In the present invention, the state of "without preliminarily contacting" is accomplished by the above contacting method at the initiation of the reaction. Further, for the additional supply of the reaction substrate and the catalyst during the reaction, the supply method is not particularly limited so long as the same contacting state is accomplished with respect to the respective materials to be supplied afresh.

By employing the above contacting method, a substantial improvement in the catalytic activities and an effect of e.g. suppressing formation of polymers, can be obtained. In the catalyst system of the present invention, a solvent-soluble component formed by the reaction of the specific chromium compound and the alkylaluminum compound is considered to have oligomerizing activities. It is considered that when the α-olefin is contacted to the specific chromium compound and the alkylaluminum compound without preliminarily contacting the specific chromium compound to either the α-olefin or the alkylaluminum compound, the resulting active species are stabilized by e.g. coordination of the α-olefin present, and the amount of the active species will increase. On the other hand, when the α-olefin is contacted after contacting the specific chromium compound to the alkylaluminum compound in the absence of the α-olefin, the amount of the active species decreases for the above reason, and reduction of the chromium compound proceeds beyond a proper reduction degree before initiation of the oligomerization reaction upon contact of the α-olefin, which are believed to be factors for deterioration of the catalytic activities. The catalytic activities deteriorate also in a case where the chromium compound and the α-olefin are preliminarily contacted and then the alkylaluminum compound is contacted thereto. In this case, it is considered that the chromium compound becomes to be hardly soluble, when reacted with the alkylaluminum compound, by the preliminary contact with the α-olefin.

Even in a case where the above contacting method is not employed, fairly high oligomerizing activities and selectivity for trimer can be obtainer by adjusting the amount of the alkylaluminum compound to the chromium compound to a level of at least 20 mmol per g of the chromium compound having at least one chromium-pyrrolyl bond or at least 100 mmol per g of chromium metal, preferably at least 30 mmol per g of the chromium compound or at least 150 mmol per g of chromium metal. If the amount of the alkylaluminum compound is less than 20 mmol per g of the chromium compound having at least one chromium-pyrrolyl bond, selectivity for trimer and catalytic activities tend to be low.

By increasing the amount of the alkylaluminum compound to the chromium compound, the solubility of the chromium compound is promoted, and the amount of active species increases. This is believed to the reason why it is possible to obtain fairly high oligomerizing activities and selectivity for trimer even when the above-mentioned contacting method is not employed. There is no particular restriction as to the upper limit for the amount of the alkylaluminum compound. However, if the alkylaluminum compound is used unnecessarily in a large amount, the yield of the product per the alkylaluminum compound decreases. The upper limit of the amount of the alkylaluminum compound is preferably 1000 mmol per g of the chromium compound having at least one chromium-pyrrolyl bond or 5000 mmol per g of chromium metal, more preferably 500 mmol per g of the chromium compound or 2500 mmol per g of chromium metal.

On the other hand, the contacting method and/or the amount of an alkylaluminum compound added in the oligomerization of an α-olefin in the present invention may not be particularly restricted by using the catalyst system which is comprised from the chromium compound prepared by the reaction of a chromium salt with a compound containing a pyrrolyl group in a hydrocarbon solvent. However, when both of either the same contacting method and/or the same amount of an alkylaluminum compound stated before are/is employed in the oligomerization of an α-olefin wherein the chromium compound is formed in a hydrocarbon solvent, the activity and the selectivity for trimer can tend to increase. (Similarly mentioned hereinbefore.) The reason why the increasement of the activity and the selectivity for trimer is considered to be the same described hereinbefore.

The concentration of the chromium compound in the oligomerization of the α-olefin in the present invention is usually from 0.1 mg to 5 g of the specific chromium compound or from 0.02 mg to 1 g of chromium metal, per l of the solvent, preferably from 1 mg to 2 g of the specific chromium compound or from 0.2 mg to 0.4 g of chromium metal, per l of the solvent. However, by adjusting the concentration preferably to a level of at most 150 mg of the chromium compound having at least one chromium-pyrrolyl bond or at most 30 mg of chromium metal, per l of the solvent, more preferably at most 100 mg of the chromium compound or at most 20 mg of chromium metal, per l of the solvent, the catalytic activities (g olefin/g chromium-hr) and the catalytic efficiency (g olefin/g chromium compound) will substantially increase. The lower limit of the concentration of the chromium compound is not particularly limited. However, if the concentration is too low, the yield of the product per reactor will be low, such being undesirable. Therefore, the lower limit is usually at a level of 20 mg of the chromium compound or 4 mg of chromium metal, per l of the solvent. The mechanism of the increase of the activities is not yet clearly understood, but it is considered that by the decrease of the concentration of the chromium compound, the solubility of the compound increases, or the association degree decreases to bring about an increase of effective active sites.

Further, in the oligomerization of an α-olefin of the present invention, an improvement in the catalytic activities and selectivity for trimer is observed when hydrogen is present during the reaction. Especially when the oligomerization reaction of the present invention is conducted in an alicyclic hydrocarbon solvent and in the presence of hydrogen, the catalytic activities and selectivity for trimer can remarkably be improved. In a case where the oligomerization reaction of an α-olefin, especially ethylene, is conducted by using a catalyst comprising the chromium compound having at least one chromium-pyrrolyl bond and an alkylaluminum, an improvement in the catalytic activities and selectivity for trimer is observed by the presence of hydrogen, but the selectivity of 1-hexene among hexenes produced tends to decrease. A feature of the present invention resides in that when the oligomerization reaction is conducted by using a catalyst comprising the specific chromium compound obtained in a hydrocarbon solvent and an alkylaluminum, not only an improvement in the catalytic activities and selectivity for trimer is obtainable, but also no substantial decrease in the selectivity of 1-hexane among hexenes produced is observed by the presence of hydrogen.

Formation of polymers (those insoluble in a hydrocarbon solvent at room temperature) in the oligomerization of an α-olefin according to the present invention, is not more than 25% by weight of the total product. According to a preferred method of the present invention, formation of such polymers, is not more than 15% by weight. By employing the proper method, it can be controlled to a level of not more than 5% by weight.

According to the method of the present invention, a product composed mainly of a trimer can be selectively obtained in good yield by oligomerizing an α-olefin, particularly ethylene, and formation of polymers can be controlled. Thus, the present invention provides a significant industrial advantage.

Further, by using as a catalyst the specific chromium compound obtained by the reaction in a hydrocarbon solvent, when an α-olefin, particularly ethylene, is oligomerized, the selectivity of 1-hexene among hexenes produced will be improved, whereby purification of 1-hexene by e.g. distillation will be easy, and the costs for the purification apparatus can be reduced. Further, a product of a high purity can be obtained without requiring a particularly precise purification operation, and the oligomerization reaction proceeds at a high catalytic activities. Therefore, the value of the method of the present invention for industrial application is high.

Now, the present invention will be described in further detail with reference to Examples. However, it should be understood that the present invention is by no means restricted by such specific Examples.

CATALYST PREPARATION EXAMPLE 1

Preparation of chromium compound 1

To 0.815 g (20.3 mmol) of NaH, 15 ml of THF was added, and 1.4 ml (20 mmol) of pyrrole dissolved in 5 ml of THF was dropwise added thereto. The mixture was stirred at room temperature for one hour, and then this solution was dropwise added to 1.23 g (10 mmol) of $CrCl_2$ suspended in 20 ml of THF. After the dropwise addition, 5 ml of THF was added thereto, and the mixture was refluxed for 20 hours under heating. The precipitate was filtered off. Then, 100 ml of pentane was added to the filtrate, and the mixture was left to stand still at 5° C. The formed precipitate was collected by filtration and dried to obtain 0.506 g of a dark green powder. The contents of elements in this powder were as follows.

Cr: 19.1%, C: 52.3%, H: 5.45%, N: 11.6%.

CATALYST PREPARATION EXAMPLE 2

Preparation of chromium compound 2

To 19 ml (30 mmol of n-BuLi) of a n-BuLi/n-hexane solution, 2.1 ml (30 mmol) of pyrrole dissolved in 20 ml of THF was dropwise added at −78° C., and the mixture was stirred for 15 minutes. Then, the mixture was returned to room temperature, and stirring was continued at room temperature for 2 hours. To this solution, 1.58 g (10 mmol) of $CrCl_3$ was added in a powder form. Then, the mixture was refluxed for 5 hours under heating. After being left to cool, the formed precipitate was filtered off. The filtrate was dried up to obtain a powder. The contents of elements in this powder were as follows.

Cr: 6.6%, C: 69.2%, H: 7.3%, N: 15.1%.

CATALYST PREPARATION EXAMPLE 3

Preparation of chromium compound 3

To 0.79 g (16.5 mmol) of NaH, 15 ml of THF was added, and 1.0 ml (15 mmol) of pyrrole dissolved in 5 ml of THF was dropwise added thereto. The mixture was stirred at room temperature for one hour, and then this solution was dropwise added to 0.79 g (5 mmol) of $CrCl_3$ suspended in 25 ml of THF. After the dropwise addition, the mixture was refluxed for 5 hours under heating. The precipitate was filtered off. Then, the solvent was distilled off to obtain 1.65 g of a black powder. The contents of elements in this powder were as follows.

Cr: 6.5%, C: 58.0%, H: 6.6%, N: 10.5%.

CATALYST PREPARATION EXAMPLE 4

Preparation of chromium compound 4

To 15 ml of a THF solution of pyrrole (10.1 mmol), MeLi (7.5 ml of a 1.4M $Et_2O$ solution, 10.5 mmol) was dropwise added at −78° C. After dropwise addition, the mixture was stirred at room temperature for 30 minutes. To the lithium pyrrolide thus obtained, a solution obtained by dissolving $CrCl_2$ $(THF)_2$ (1.33 g, 4.82 mmol) in 5 ml of THF, was added at room temperature, and the mixture was stirred for 3 hours, whereby the reaction solution turned black. The reaction solution was filtered through a G3 filter, and the filtrate was concentrated to obtain a black powder. Then, 10 ml of toluene and 3 ml of pyridine were added thereto, and the mixture was heated by an oil bath and filtered through a G3 filter while it was still hot. The obtained filtrate was slowly cooled to room temperature. The supernatant of precipitated needle-like crystals was removed, and the crystals were washed with toluene to obtain 593.6 g of brown needle-like crystals. The obtained crystals were pulverized and used for the oligomerization reaction. The contents of elements in the needle-like crystals were as follows.

Cr: 10 0%, C: 69 2% H: 6 06%, N: 13 7%

CATALYST PREPARATION EXAMPLE 5

Preparation of chromium compound 5

To 12 ml of a THF solution (0.5 M) of Na (pyrrolide), a THF suspension (8 ml) of $CrCl_3.3$ pyridine (0.79 g, 2 mmol) was dropwise added at room temperature. The mixture was stirred for one hour and then refluxed for 5 hours. After cooling the mixture to room temperature, 10 ml of THF was added thereto, and the supernatant was transferred by a syringe. This operation was repeated twice, and the obtained brown solution was concentrated to obtain 340 mg of a brown powder.

CATALYST PREPARATION EXAMPLE 6

Preparation of chromium compound 6

To a solution of chromium (III) acetylacetonate (2.55 g, 7.3 mmol) in toluene (15 ml), a suspension of powdery lithium pyrrolide (1.60 g, 21.9 mmol) separately prepared, in toluene (5 ml), was added at room temperature under a nitrogen atmosphere. The reaction mixture was gradually heated to 100° C., and the stirring was continued for 25 hours while maintaining the temperature. The reaction mixture was cooled to room temperature, and then the solvent was distilled off under reduced pressure from the reaction mixture, to obtain 4.15 g of a reddish brown powder. For the oligomerization reaction of ethylene, this powder was used as it was. The results of the elemental analysis of this powder was as shown below. The yield per Cr as calculated from the analyzed value of Cr and the obtained amount, was 100%. The IR spectrum of this powder is shown in FIG. 1. The measurement was conducted by a nujor method using 165 Model FT-IR, manufactured by Perkin Elmer.

Cr: 9.1%, C: 57.0%, H: 5.9%, N: 7.4%.

CATALYST PREPARATION EXAMPLE 7

Preparation of chromium compound 7

TO a solution of chromium (III) (2-ethylhexanoate) (1.14 g, 2.36 mmol) in toluene (15 ml), a suspension of powdery sodium pyrrolide (0.65 g, 7.26 mmol) separately prepared, in toluene (5 ml), was added at room temperature under a nitrogen atmosphere. Ultrasonic waves were irradiated to the reaction mixture for 17 hours. During this period, the water temperature of the ultrasonic wave cleaning apparatus rose to a level of 40° C. After completion of the reaction, the supernatant was withdrawn to remove unreacted chromium (III) (2-ethylhexanoate). Then, the residue was washed with heptane, and the supernatant was removed in the same manner as above. The residual solid was vacuum-dried at room temperature to obtain 0.97 g of a deep green powder. The results of the elemental analysis of this powder were as follows. The yield per Cr as calculated from the analytical value of Cr and the obtained amount, was 83.7%.

Cr: 7.5%, C: 58.1%, H: 7.4%, N: 7.2%.

EXAMPLE 1

A 300 ml autoclave heat-dried by a drier at 150° C., was assembled while it was still hot, and flushed with nitrogen under vacuum. This autoclave was provided with a catalyst feed tube equipped with a burst plate. 50 ml of heptane and 0.4 mmol of triethylaluminum were charged to the body side of the autoclave. On the other hand, 10 mg of chromium compound 1 slurried in 1 ml of heptane was charged to the catalyst feed tube. At such a time, the chromium compound and the triethylaluminum were not in contact to each other.

The autoclave was heated to 80° C., and ethylene was introduced at 80° C. through the catalyst feed tube. By the ethylene pressure, the burst plate bursted, whereupon the ethylene, the chromium catalyst and the triethylaluminum were simultaneously contacted to one another, and oligomerization of ethylene was initiated. Ethylene was introduced until the total pressure became 40 $kg/cm^2$, and thereafter oligomerization of ethylene was conducted for one hour while maintaining the total pressure at 40 $kg/cm^2$. The internal temperature of the autoclave became 90° C. by the polymerization heat, and thereafter the reaction temperature was maintained at 90° C. One hour later, ethanol was injected to terminate the reaction, and the product was quantified by gas chromatography. The results are shown in Table 2.

EXAMPLE 2

Into the same autoclave as used in Example 1, 10 mg of the chromium compound 1 and 0.4 mmol of triethylaluminum were charged in the same manner.

Hydrogen was introduced to 3.5 kg/cm$^2$, and the autoclave was heated to 90° C. At such a time, the chromium compound and the triethylaluminum were not in contact with each other. Then, ethylene was introduced at 90° C. through the catalyst feed tube. The burst plate bursted by the ethylene pressure, whereupon the ethylene, the chromium compound and the triethylaluminum were contacted simultaneously to one another, and polymerization of ethylene was initiated. Ethylene was introduced until the total pressure became 40 kg/cm$^2$ and thereafter polymerization of ethylene was conducted for 0.5 hour while maintaining the total pressure at 40 kg/cm$^2$. The internal temperature of the autoclave became 110° C. by the polymerization heat. The autoclave was cooled and thereafter the reaction temperature was maintained at 100° C. 0.5 Hour later, ethanol was injected to terminate the reaction, and the product was quantified by gas chromatograph. The results are shown in Table 2.

EXAMPLES 3 to 8

The reaction was conducted in the same manner as in Example 1 except that the reaction conditions and the chromium compound were changed as identified in Table 1. The results are shown in Table 2.

EXAMPLE 9

Into the same autoclave as used in Example 1, 10 mg of the chromium compound as used in Example 1 and then 62 ml of heptane, were charged. Then, the temperature was raised to 90° C., and ethylene was introduced to 35 kg/cm$^2$. No absorption of ethylene was observed. Therefore, 0.4 mmol of triethylaluminum was injected, whereupon absorption of ethylene started. 30 Minutes later, ethanol was injected to terminate the reaction. The reaction temperature was maintained at 90° C. The results are shown in Table 2.

EXAMPLE 10

Oligomerization of ethylene was conducted in the same manner as in Example 7 except that the reaction solvent was changed to cyclohexane. The reaction conditions are shown in Table 1, and the results are shown in Table 2.

EXAMPLE 11

Oligomerization of ethylene was conducted in the same manner as in Example 10 except that the amount of triethylaluminum was changed to 0.4 mmol, and hydrogen was introduced to 3.5 kg/cm$^2$. The reaction conditions are shown in Table 1, and the results are shown in Table 2.

EXAMPLES 12 to 14

The reaction was conducted in the same manner as in Example 1 except that the reaction conditions and the chromium compound were changed as identified in Table 3. The results are shown in Table 3.

EXAMPLE 15

A 300 ml autoclave heat-dried by a drier at 150° C., was assembled while it was still hot, and flushed with nitrogen under vacuum. This autoclave was provided with a catalyst feed tube equipped with a burst plate. 150 ml of heptane and 0.2 mmol of triethylaluminum were charged to the body side of the autoclave. On the other hand, 10 mg of chromium compound 3 slurried in 1 ml of heptane was charged to the catalyst feed tube.

The autoclave was heated to 90° C., and ethylene was introduced at 90° C. from the catalyst feed tube. The burst plate bursted by the ethylene pressure, whereupon the ethylene, the chromium catalyst and the triethylaluminum were contacted simultaneously to one another, and oligomerization of ethylene was initiated. Ethylene was introduced until the total pressure became 35 kg/cm$^2$, and thereafter oligomerization of ethylene was conducted for one hour while maintaining the total pressure at 35 kg/cm$^2$. The internal temperature of the autoclave became 100° C. by the polymerization heat, and thereafter the reaction temperature was maintained at 100° C. One hour later, ethanol was injected to terminate the reaction, and the reaction product was quantified by gas chromatograph. The results are shown in Table 3.

EXAMPLE 16

Into the same autoclave as used in Example 15, 10 mg of chromium compound 4 prepared in Catalyst Preparation Example 4, 150 ml of heptane and 0.4 mmol of triethylaluminum were charged.

Hydrogen was introduced to 3.5 kg/cm$^2$, and the autoclave was heated to 90° C. Then, ethylene was introduced at 90° C. from the catalyst feed tube. The burst plate bursted by the ethylene pressure, whereupon the ethylene, the chromium compound and the triethylaluminum were contacted simultaneously to one another, and polymerization of ethylene was initiated. Ethylene was introduced until the total pressure became 40 kg/cm$^2$, and thereafter polymerization of ethylene was conducted for 1.0 hour while maintaining the total pressure at 40 kg/cm$^2$. The internal temperature of the autoclave became 110° C. by the polymerization heat. The autoclave was cooled, and thereafter the reaction temperature was maintained at 100° C. One hour later, ethanol was injected to terminate the reaction, and the product was quantified by gas chromatograph. The results are shown in Table 3.

EXAMPLES 17 and 18

The reaction was conducted in the same manner as in Example 15 except that as the chromium compound, chromium compound 5 obtained in Catalyst Preparation Example 5 was used, and the reaction conditions were changed as identified in Table 3. The results are shown in Table 3.

EXAMPLE 19

A 300 ml autoclave heat-dried by a drier at 150° C., was assembled while it was still hot, and flushed with nitrogen under vacuum. This autoclave was provided with a catalyst feed tube equipped with a burst plate. 50 ml of heptane and 0.4 mmol of triethylaluminum were charged to the body side of the autoclave. On the other hand, 10 mg of chromium compound 6 obtained in Catalyst Preparation Example 6 slurried in 1 ml of heptane, was charged to the catalyst feed tube. The autoclave was heated to 100° C., and ethylene was introduced at 100° C. from the catalyst feed tube. The burst plate bursted by the ethylene pressure, whereupon the ethylene, the chromium compound and the triethylaluminum were contacted simultaneously to one another, and oligomerization of ethylene was initiated. Ethylene was introduced until the total pressure became 35 kg/cm², and thereafter the total pressure was maintained at 35 kg/cm², and the reaction temperature was maintained at 100° C. One hour later, ethanol was injected to terminate the reaction, and the reaction product was quantified by gas chromatograph. The results are shown in Table 4.

EXAMPLE 20

Into the same autoclave as used in Example 19, 7 mg of chromium compound 6 obtained in Catalyst Preparation Example 6 and 0.28 mmol of triethylaluminum were charged in the same manner. Hydrogen was introduced to 3.5 kg/cm², and the autoclave was heated to 100° C. Then, ethylene was introduced at 100° C. from the catalyst feed tube. The burst plate bursted by the ethylene pressure, whereupon the ethylene, the chromium compound and the triethylaluminum were contacted simultaneously to one another, and oligomerization of ethylene was initiated. Ethylene was introduced until the total pressure became 40 kg/cm², and thereafter the total pressure was maintained at 40 kg/cm² and the reaction temperature was maintained at 100° C. One hour later, ethanol was injected to terminate the reaction, and the product was quantified by gas chromatograph. The results are shown in Table 4.

EXAMPLES 21, 23 and 24

The reaction was conducted in the same manner as in Example 19 except that the reaction conditions and the chromium compound were changed as identified in Table 4. The results are shown in Table 4.

EXAMPLE 22

The reaction was conducted in the same manner as in Example 19 except that the amount of heptane was changed to 150 ml. The results are shown in Table 4.

COMPARATIVE EXAMPLE 1

The reaction was conducted in the same manner as in Example 9 except that the amount of heptane was changed to 62 ml and the amount of triethylaluminum was changed to 0.12 mmol. The results are shown in Table 2 (continued).

COMPARATIVE EXAMPLE 2

The reaction was conducted in the same manner as in Comparative Example 1 except that 3.5 kg/cm² of hydrogen was introduced prior to the introduction of triethylaluminum, and the total pressure was 40 kg/cm². The results are shown in Table 2.

COMPARATIVE EXAMPLE 3

The reaction was conducted in the same manner as in Comparative Example 1 except that into the autoclave, triethylaluminum and the chromium compound were charged in a heptane solvent and heat-treated at 90° C. for 30 minutes, and then ethylene was introduced, and the reaction temperature was changed to 100° C. The results are shown in Table 2.

TABLE 1

| No. | | Examples | | | | | | | | | | | Comparative Examples | | |
|---|---|---|---|---|---|---|---|---|---|---|---|---|---|---|---|
| | | 1 | 2 | 3 | 4 | 5 | 6 | 7 | 8 | 9 | 10 | 11 | 1 | 2 | 3 |
| Cr compound | | 1 | 1 | 1 | 1 | 1 | 2 | 3 | 1 | 1 | 3 | 3 | 1 | 1 | 1 |
| Amount of Cr compound | mg | 10 | 10 | 10 | 10 | 10 | 10 | 10 | 10 | 10 | 10 | 10 | 10 | 10 | 10 |
| Amount of solvent | ml | 50 | 50 | 50 | 50 | 50 | 50 | 50 | 50 | 62 | 50 | 50 | 50 | 50 | 50 |
| Concentration of Cr compound | mg/l | 200 | 200 | 200 | 200 | 200 | 200 | 200 | 200 | 161 | 200 | 200 | 200 | 200 | 200 |
| Amount of triethylaluminum | mmol | 0.4 | 0.4 | 0.4 | 0.2 | 5.0 | 0.2 | 0.2 | 0.12 | 0.4 | 0.2 | 0.4 | 0.12 | 0.12 | 0.12 |
| | mmol/chromium compound (g) | 40 | 40 | 40 | 20 | 500 | 20 | 20 | 12 | 40 | 20 | 40 | 12 | 12 | 12 |
| Contacting method | | A | A | A | A | A | A | A | A | B | A | A | B | B | C |
| Amount of H₂ | kg/cm² | 0 | 3.5 | 0 | 0 | 0 | 0 | 0 | 0 | 0 | 0 | 3.5 | 0 | 3.5 | 0 |
| Total Pressure | kg/cm² | 40 | 40 | 35 | 35 | 35 | 35 | 35 | 35 | 35 | 35 | 40 | 35 | 40 | 35 |
| Reaction temperature | °C. | 90 | 100 | 100 | 100 | 100 | 100 | 100 | 100 | 90 | 100 | 100 | 90 | 90 | 100 |
| Reaction time | hr | 1.0 | 0.5 | 0.5 | 1.0 | 0.58 | 1.0 | 1.0 | 1.0 | 0.5 | 1.0 | 1.0 | 0.5 | 0.5 | 0.5 |
| Solvent | | | | | Heptane | | | | | Heptane | Cyclohexane | | | Heptane | |

Note:
Contacting methods
A: Three components of ethylene, chromium compound and triethylaluminum are contacted simultaneously.
B: Ethylene and chromium compound are contacted and heated, and then, triethylaluminum is contacted.
C: Chromium compound and triethylaluminum are heat-treated and then contacted to ethylene.

TABLE 2

| No. | | | Examples | | | | | | | | | | | Comparative Examples | | |
|---|---|---|---|---|---|---|---|---|---|---|---|---|---|---|---|---|
| | | | 1 | 2 | 3 | 4 | 5 | 6 | 7 | 8 | 9 | 10 | 11 | 1 | 2 | 3 |
| Amount of formed olefins | | g | 10.99 | 17.9 | 8.84 | 7.65 | 11.7 | 6.66 | 4.27 | 4.24 | 3.69 | 8.16 | 24.10 | 0.79 | 0.98 | 0.60 |
| Composition (wt %) | $C_4$ | | 19.2 | 11.5 | 23.6 | 19.0 | 20.3 | 22.0 | 23.3 | 15.7 | 11.8 | 18.5 | 5.9 | 1.40 | 3.10 | 8.26 |
| | $C_6$ | Total | 55.4 | 75.8 | 55.5 | 58.4 | 55.8 | 61.9 | 56.7 | 58.5 | 58.6 | 64.7 | 86.9 | 24.3 | 48.2 | 78.7 |
| | | 1-$C_6$ content | 92.6 | 88.5 | 91.0 | 85.9 | 90.0 | 86.3 | 92.2 | 87.8 | 87.5 | 93.1 | 85.3 | 91.7 | 88.3 | 85.0 |
| | $C_8$ | | 9.7 | 5.1 | 9.0 | 7.7 | 9.9 | 8.0 | 8.2 | 6.2 | 3.8 | 7.8 | 3.2 | 0.3 | 1.1 | tr. |
| | $C_{10}$–$C_{20}$ | | 11.2 | 6.7 | 10.2 | 9.7 | 13.7 | 8.0 | 10.5 | 6.8 | 3.0 | 8.2 | 3.7 | tr. | 1.7 | tr. |
| | $C_{22}$–$C_{30}$ | | 0 | 0.1 | 0.2 | 0.4 | 0.2 | 0.1 | 0.4 | 0.1 | 0 | 0.2 | 0.1 | 0 | 0.5 | 0 |
| | PE | | 4.5 | 0.8 | 1.5 | 4.8 | 0.1 | 0 | 0.9 | 12.7 | 22.8 | 0.6 | 0.3 | 74.0 | 45.4 | 5.1 |
| Catalytic efficiency | g olefin/ g Cr compound | | 1,100 | 1,790 | 884 | 765 | 1,170 | 666 | 427 | 424 | 369 | 816 | 2,410 | 79 | 98 | 60 |
| Catalytic activity | g olefin/ g Cr · hr | | 5,760 | 18,700 | 9,260 | 4,000 | 10,500 | 10,100 | 6,570 | 2,220 | 3,860 | 12,550 | 37,080 | 830 | 1,030 | 628 |

TABLE 3

| No. | | 12 | 13 | 14 | 15 | 16 | 17 | 18 |
|---|---|---|---|---|---|---|---|---|
| Cr compound | | 4 | 5 | 5 | 3 | 4 | 5 | 5 |
| Amount of Cr compound | mg | 30 | 30 | 30 | 10 | 10 | 10 | 5 |
| Amount of solvent | ml | 50 | 50 | 150 | 150 | 150 | 150 | 150 |
| Concentration of Cr compound | mg/l | 600 | 600 | 200 | 67 | 67 | 67 | 33 |
| Amount of triethylaluminum | mmol | 1.2 | 1.2 | 1.2 | 0.2 | 0.4 | 0.4 | 0.2 |
| Amount of $H_2$ | kg/cm² | 0 | 0 | 0 | 0 | 3.5 | 0 | 0 |
| Total Pressure | kg/cm² | 35 | 35 | 35 | 35 | 40 | 35 | 35 |
| Reaction temperature | °C. | 100 | 100 | 100 | 100 | 100 | 100 | 100 |
| Reaction time | hr | 1.0 | 1.0 | 1.0 | 1.0 | 1.0 | 1.0 | 1.0 |
| Amount of | g | 13.82 | 10.06 | 16.6 | 7.43 | 33.17 | 11.21 | 6.38 |
| Composition (wt %) | $C_4$ | 17.2 | 16.6 | 15.5 | 16.8 | 12.5 | 15.5 | 17.2 |
| | $C_6$ | 60.9 | 65.7 | 66.3 | 64.4 | 75.9 | 65.8 | 64.5 |
| | $C_8$ | 10.2 | 8.8 | 8.8 | 8.8 | 5.7 | 8.9 | 8.9 |
| | $C_{10}$–$C_{20}$ | 11.5 | 8.9 | 9.3 | 9.3 | 5.9 | 9.7 | 0.1 |
| | $C_{22}$–$C_{30}$ | 0.2 | 0.1 | tr. | 0.2 | 0.1 | 0.1 | tr. |
| | PE | tr. | tr. | tr. | 0.5 | 0 | tr. | tr. |
| Catalytic efficiency | g olefin/ g Cr compound | 460 | 335 | 553 | 743 | 3,320 | 1,120 | 1,276 |
| Catalytic activity | g olefin/ g Cr · hr | 4,590 | — | — | 11,400 | 33,100 | — | — |

TABLE 4

| No. | | 19 | 20 | 21 | 22 | 23 | 24 |
|---|---|---|---|---|---|---|---|
| Cr compound | | 6 | 6 | 6 | 6 | 6 | 7 |
| Amount of Cr compound | mg | 10 | 7 | 10 | 10 | 10 | 10 |
| Amount of triethylaluminum | mmol | 0.4 | 0.28 | 0.8 | 0.4 | 0.2 | 0.4 |
| Amount of $H_2$ | kg/cm² | 0 | 3.5 | 0 | 0 | 0 | 0 |
| Total Pressure | kg/cm² | 35 | 40 | 35 | 35 | 35 | 35 |
| Reaction temperature | °C. | 100 | 100 | 100 | 100 | 100 | 100 |
| Reaction time | hr | 1 | 1 | 1 | 1 | 1 | 1 |
| Amount of formed olefins | g | 4.70 | 7.23 | 4.07 | 4.71 | 1.03 | 1.90 |
| Composition (wt %) | $C_4$ | 10.1 | 6.3 | 13.5 | 11.8 | 9.2 | 10.3 |
| | $C_6$ Total | 55.0 | 67.6 | 64.5 | 57.3 | 62.5 | 77.4 |
| | 1-$C_6$ | 93.7 | 92.2 | 93.6 | 93.7 | 93.5 | 93.8 |
| | $C_8$ | 8.9 | 6.3 | 8.6 | 9.3 | 3.9 | 5.1 |
| | $C_{10}$–$C_{20}$ | 21.1 | 15.5 | 12.9 | 19.6 | 8.8 | 4.8 |
| | $C_{22}$–$C_{30}$ | 2.8 | 2.5 | 0.4 | 2.0 | 2.4 | 0 |
| | PE | 2.1 | 1.8 | 0.1 | tr. | 13.1 | 2.4 |
| Catalytic efficiency | g olefin/ g Cr compound | 470 | 1,033 | 407 | 471 | 103 | 190 |
| Catalytic | g olefin/ | 5,165 | 11,352 | 4,460 | 5,176 | 1,131 | 2,533 |

TABLE 4-continued

| | | Examples | | | | | |
|---|---|---|---|---|---|---|---|
| No. | | 19 | 20 | 21 | 22 | 23 | 24 |
| activity | g Cr-hr | | | | | | |

What is claimed is:

1. A method for oligomerizing an α-olefin in the presence of a catalyst comprising a chromium compound having at least one chromium-pyrrolyl bond and an alkylaluminum compound, comprising the steps of:
    (a) contacting the α-olefin with the chromium compound and the alkylaluminum compound simultaneously without preliminarily contacting the chromium compound with either the α-olefin or the alkylaluminum compound,
    (b) oligomerizing the α-olefin at a temperature of from 0° to 250° C. under a pressure from atmospheric pressure to 250 kg/cm², and the concentration of the chromium compound is from 0.1 mg to 5 g per liter of solvent, and the alkylaluminum compound is in an amount of at least 5 mmol per gram of the chromium compound.

2. The method for oligomerizing an α-olefin according to claim 1, wherein the chromium compound, the α-olefin and the alkylaluminum compound are supplied to a reactor.

3. The method for oligomerizing an α-olefin according to claim 2, comprising supplying to a reactor the chromium compound, the α-olefin and the alkylaluminum compound directly and independently.

4. The method for oligomerizing an α-olefin according to claim 1, comprising contacting the chromium compound, the alkylaluminum compound and the α-olefin to form a mixture, and the mixture is then supplied to a reactor.

5. The method for oligomerizing an α-olefin according to claim 1, wherein the alkylaluminum compound is present in an amount of at least 5 mmol per g of the chromium compound.

6. The method for oligomerizing an α-olefin according to claim 1, wherein the alkylaluminum compound is present in an amount of at least 25 mmol per g of chromium atoms.

7. A method for oligomerizing an α-olefin in the presence of a catalyst comprising a chromium compound having at least one chromium-pyrrolyl bond and an alkylaluminum compound, comprising contacting the α-olefin with the chromium compound and the alkylaluminum compound without preliminarily contacting the chromium compound with either the α-olefin or the alkylaluminum compound, and wherein as the catalyst, a catalyst comprising a chromium compound obtained by reacting a chromium salt and a compound containing a pyrrolyl group or radical in a hydrocarbon solvent, and an alkyl aluminum compound, is used wherein the oligomerization is conducted at a temperature of from 0° to 250° C. under a pressure from atmospheric pressure to 250 kg/cm², and the concentration of the chromium compound is from 0.1 mg to 5 q per liter of the solvent, and the alkylaluminum compound is in an amount of at least 0.1 mmol per gram of the chromium compound.

8. The method for oligomerizing an α-olefin according to claim 7, wherein the chromium salt is selected from the group consisting of a chromium β-diketonate, a chromium carboxylate, a chromium β-ketocarboxylate, a chromium-amide complex, a chromium-carbonyl complex, a chromium-cyclopentadienyl complex, a chromium-alkyl complex and a chromium-phenyl complex.

9. The method for oligomerizing an α-olefin according to claim 7, wherein said solvent is selected from the group consisting of a hydrocarbon compound and a halogenated hydrocarbon compound.

10. A method for oligomerizing an α-olefin in the presence of a catalyst comprising a chromium compound having at least one chromium-pyrrolyl bond and an alkylaluminum compound, comprising contacting the α-olefin with the chromium compound and the alkylaluminum compound without preliminarily contacting the chromium compound with either the α-olefin or the alkylaluminum compound, and wherein the chromium compound having at least one chromium-pyrrolyl bond is a compound obtained by reacting a chromium salt of the formula $CrX_n$ wherein X is an organic or inorganic group, and n is an integer of from 1 to 6, provided that when n is more than 1, the plurality of X may be the same or different from one another, and a metal pyrrolide in an electron pair donor solvent, comprising oligomerizing the e-olefin at a temperature of from 0° to 250° C. under a pressure from atmospheric pressure to 250 kg/cm², and the concentration of the chromium compound is from 0.1 mg to 5 g per liter of the solvent, and the alkylaluminum compound is an amount of at least 5 mmol per gram of the chromium compound.

11. The method for oligomerizing an α-olefin according to claim 10, wherein the alkylaluminum compound is present in an amount of at least 20 mmol per g of the chromium compound.

12. The method for oligomerizing an α-olefin according to claim 10, wherein the organic group is selected from the group consisting of a $C_{1-30}$ hydrocarbon group, a carbonyl group, an alkoxy group, a carboxyl group, a β-diketonate group, a β-ketocarboxyl group, a β-ketoester group and an amide group.

13. The method for oligomerizing an α-olefin according to claim 10, wherein the inorganic group is selected from the group consisting of a halogen, nitrate, sulfate and an oxide.

14. The method for oligomerizing an α-olefin according to claim 10, wherein the chromium salt is a halogenated chromium.

15. The method for oligomerizing an α-olefin according to claim 10, wherein the metal pyrrolide is a pyrrolide of a metal selected from the group consisting of elements of Groups IA, IIA, IIIB and IVB of the Periodic Table.

16. The method for oligomerizing an α-olefin according to claim 10, wherein the electron pair donor solvent is a solvent containing an element selected from the group consisting of N, O, P and S.

17. The method for oligomerizing an α-olefin according to claim 10, wherein the electron pair donor solvent is an ether.

18. The method for oligomerizing an α-olefin according to claim 1 or 7, wherein the alkyl aluminum compound is a compound of the formula (1):

$$R^1{}_m Al(OR^2)_n H_p X_q \qquad (1)$$

wherein each of $R^1$ and $R^2$ which may be the same or different, is a $C_{1-15}$ hydrocarbon group, X is a halogen atom, $0<m\leq3$, $0\leq n<3$, $0\leq p<3$, $0\leq q<3$, and $m+n+p+q=3$.

19. The method for oligomerizing an α-olefin according to claim 1 or 7, wherein the α-olefin has from 2 to 30 carbon atoms.

20. The method for oligomerizing an α-olefin according to claim 19, wherein the α-olefin is ethylene, and the main product is 1-hexene.

21. The method for oligomerizing an α-olefin according to claim 1 or 7, wherein the oligomerization is conducted in a solvent selected from the group consisting of a chain saturated hydrocarbon and an alicyclic hydrocarbon.

22. The method for oligomerizing an α-olefin according to claim 1 or 7, wherein the oligomerization reaction is conducted in the presence of hydrogen.

23. A method for oligomerizing an α-olefin in the presence of a catalyst comprising a chromium compound and an alkylaluminum compound, wherein as the catalyst, a catalyst comprising a chromium compound obtained by admixing a chromium salt and a compound containing a pyrrolyl group or radical in a hydrocarbon solvent, and an alkyl aluminum compound, is used, and comprising the steps of:

(a) contacting the α-olefin with the chromium compound and the alkylaluminum compound simultaneously without preliminarily contacting the chromium compound with either the α-olefin or the alkylaluminum compound, (b) oligomerizing the α-olefin at a temperature of from 0° to 250° C. under a pressure from atmospheric pressure to 250 kg/cm$^2$, and the concentration of the chromium compound is from 0.02 mg to 1 g of chromium metal per liter of solvent, and said alkylaluminum compound is in an amount of at least 0.1 mmol per gram of the chromium compound.

24. A process according to claim 1, wherein the molar ratio of (a) a chromium salt, to (b) a compound containing a pyrrolyl group or radical is 1:2 to 1:3.

25. A method for oligomerizing an α-olefin in the presence of a catalyst comprising a chromium compound having at least one chromium-pyrrolyl bond and an alkylaluminum compound, comprising the steps of:

(a) contacting the α-olefin with the alkylaluminum compound without preliminarily contacting the chromium compound with either the α-olefin or the alkylaluminum compound, (b) contacting the chromium compound with the α-olefin and the alkylaluminum compound, and (c) oligomerizing the α-olefin at a temperature of from 0° to 250° C. under a pressure from atmospheric pressure to 250 kg/cm$^2$, and the concentration of the chromium compound is from 0.1 mg to 5 g per liter of solvent, and the alkylaluminum compound is in an amount of at least 5 mmol per gram of the chromium compound.

26. A method for oligomerizing an α-olefin in the presence of a catalyst comprising a chromium compound and an alkylaluminum compound, wherein as the catalyst, a catalyst comprising a chromium compound obtained by admixing a chromium salt and a compound containing a pyrrolyl group or radical in a hydrocarbon solvent, and an alkyl aluminum compound, is used, and comprising the steps of:

(a) contacting the α-olefin with the alkylaluminum compound without preliminarily contacting the chromium compound with either the α-olefin or the alkylaluminum compound, (b) contacting the chromium compound with the α-olefin and the alkylaluminum compound, and (c) oligomerizing the α-olefin at a temperature of from 0° to 250° C. under a pressure from atmospheric pressure to 250 kg/cm$^2$, and the concentration of the chromium compound is from 0.02 mg to 1 g of chromium metal per liter of solvent, and said alkylaluminum compound is in an amount of at least 0.1 mmol per gram of the chromium compound.

27. The method for oligomerizing an α-olefin according to claim 23, wherein the chromium compound, the α-olefin and the alkylaluminum compound are supplied to a reactor.

28. The method for oligomerizing an α-olefin according to claim 23, comprising supplying to a reactor the chromium compound the α-olefin and the alkylaluminum compound, directly and independently.

29. The method for oligomerizing an α-olefin according to claim 23, comprising contacting the chromium compound, the alkylaluminum compound and the α-olefin to form a mixture, and the mixture is then supplied to a reactor.

30. The method for oligomerizing an α-olefin according to claim 25, wherein the chromium compound, the α-olefin and the alkylaluminum compound are supplied to a reactor.

31. The method for oligomerizing an α-olefin according to claim 25, wherein contacting step (b) forms a mixture, and the mixture is supplied to a reactor.

32. The method for oligomerizing an α-olefin according to claim 26, wherein the chromium compound, the α-olefin and the alkylaluminum compound are supplied to a reactor.

33. The method for oligomerizing an α-olefin according to claim 26, wherein contacting step (b) forms a mixture, and the mixture is then supplied to a reactor.

* * * * *